United States Patent
Thomas et al.

(10) Patent No.: US 9,193,504 B2
(45) Date of Patent: Nov. 24, 2015

(54) MEDICAL DOCUMENT ATTACHMENT DEVICE

(71) Applicant: Aesculap AG, Tuttlingen (DE)

(72) Inventors: Stefan Thomas, Tuttlingen (DE); John Gray-Dreizler, Rottweil (DE); Wilhelm Gleichauf, Tuttlingen-Moehringen (DE); Mariana Jakab, Tuttlingen (DE); Stefan Schuster, Villingen-Schwenningen (DE)

(73) Assignee: Aesculap AG, Tuttingen (DE)

( * ) Notice: Subject to any disclaimer, the term of this patent is extended or adjusted under 35 U.S.C. 154(b) by 0 days.

(21) Appl. No.: 14/031,181

(22) Filed: Sep. 19, 2013

(65) Prior Publication Data

US 2014/0091089 A1    Apr. 3, 2014

(30) Foreign Application Priority Data

Oct. 1, 2012 (DE) .......................... 10 2012 109 302

(51) Int. Cl.
| | |
|---|---|
| *B65D 51/24* | (2006.01) |
| *A61L 2/00* | (2006.01) |
| *B65D 25/20* | (2006.01) |
| *A61L 9/00* | (2006.01) |
| *A61L 2/26* | (2006.01) |

(52) U.S. Cl.
CPC ............... *B65D 25/205* (2013.01); *A61L 2/00* (2013.01); *A61L 2/26* (2013.01); *A61L 9/00* (2013.01); *B65D 51/245* (2013.01); *A61L 2202/182* (2013.01); *B65D 2251/06* (2013.01)

(58) Field of Classification Search
CPC ............. B65D 25/205; B65D 2251/06; B65D 51/245; A61L 2/00; A61L 2/26; A61L 9/00; A61L 2202/182
USPC ................ 220/212, 212.5, 318, 729; 40/311; 292/DIG. 11
See application file for complete search history.

(56) References Cited

U.S. PATENT DOCUMENTS

| | | | | | |
|---|---|---|---|---|---|
| 846,111 | A | * | 3/1907 | Kannenberg | 220/318 |
| 1,207,974 | A | * | 12/1916 | Miller | 292/288 |
| 2,536,246 | A | * | 1/1951 | Wendt | 99/349 |
| 2,768,851 | A | * | 10/1956 | Gifford | 292/30 |
| 2,974,990 | A | * | 3/1961 | Mereness | 292/288 |
| 3,312,373 | A | * | 4/1967 | Gentry | 222/131 |
| 4,330,050 | A | * | 5/1982 | Sangster et al. | 190/110 |

(Continued)

FOREIGN PATENT DOCUMENTS

| | | |
|---|---|---|
| DE | 92 12 315 | 1/1993 |
| DE | 10 2010 037 659 | 3/2012 |

*Primary Examiner* — Fenn Mathew
*Assistant Examiner* — James N Smalley
(74) *Attorney, Agent, or Firm* — Lipsitz & McAllister, LLC (57) ABSTRACT

The invention relates to a medical document attachment device for a medical sterilization container. The document attachment device comprises a sterilization container lid having an upper side, and at least one document holder having a first attachment portion and spaced therefrom a second attachment portion and a clamping portion arranged between the first attachment portion and the second attachment portion, the first attachment portion and the second attachment portion being fixed to the sterilization container lid when the document holder is connected to the sterilization container lid, and there being arranged between the clamping portion and the upper side of the sterilization container lid a document receptacle in which a document is fixable in a clamped manner by means of the clamping portion on the upper side.

23 Claims, 5 Drawing Sheets

(56) References Cited

U.S. PATENT DOCUMENTS

| | | | |
|---|---|---|---|
| 5,287,982 A * | 2/1994 | Tsai | 220/212.5 |
| 5,372,787 A | 12/1994 | Ritter | |
| 5,887,716 A | 3/1999 | Williams et al. | |
| 6,138,831 A * | 10/2000 | Agostinelli | 206/541 |
| 2005/0097710 A1 * | 5/2005 | Johnson | 24/300 |
| 2006/0162210 A1 | 7/2006 | Bauer | |
| 2011/0192744 A1 | 8/2011 | Parker et al. | |
| 2013/0175276 A1 | 7/2013 | Gleichauf et al. | |

* cited by examiner

FIG.5

MEDICAL DOCUMENT ATTACHMENT DEVICE

This application claims the benefit of German application number 10 2012 109 302.4 filed on Oct. 1, 2012, which is incorporated herein by reference in its entirety and for all purposes.

BACKGROUND OF THE INVENTION

The invention relates to a medical document attachment device for a medical sterilization container.

Medical sterilization containers are used for sterilizing sterilization articles such as, for example, surgical instruments. The sterilization articles are arranged loosely or accommodated in a medical perforated basket in a receiving space of the sterilization container, which is formed by a sterilization container tub and a sterilization container lid. In order to label the sterilization articles, it is known to provide on the sterilization container tub a small receptacle into which a small sign or label containing information on the sterilization articles can be inserted. Other sterilization containers have on an end face next to a handle element and a closure element for closing the sterilization container lid on the sterilization container tub a holder for securing a small label. In yet again different sterilization containers, small labels are attached by means of a band to a handle element of the sterilization container, and, furthermore, it is known to provide information relating to the sterilization articles on a seal which is used when sealing the sterilization container. A disadvantage of the known solutions is, in each case, the handling of the small labels or the seal. Also, in the known solutions, only a small amount of information relating to the sterilization articles can be affixed to the sterilization container.

The object of the present invention is to provide a medical document attachment device for a medical sterilization container, which is easy to handle.

SUMMARY OF THE INVENTION

This object is accomplished, in accordance with the invention, by a medical document attachment device for a medical sterilization container, which is characterized by a sterilization container lid having an upper side, and at least one document holder having a first attachment portion and spaced therefrom a second attachment portion and a clamping portion arranged between the first attachment portion and the second attachment portion, the first attachment portion and the second attachment portion being fixed to the sterilization container lid when the document holder is connected to the sterilization container lid, and there being arranged between the clamping portion and the upper side of the sterilization container lid a document receptacle in which a document is fixable in a clamped manner by means of the clamping portion on the upper side.

With the document attachment device in accordance with the invention, a document containing information on the sterilization container or sterilization articles accommodated therein can be attached to an upper side of the sterilization container lid in a way which is easy to handle. "Upper side" is to be understood, in the present case, as referring to a position of use of the sterilization container lid in which it is placed in accordance with the intended use on a sterilization container tub of the sterilization container. At least one document holder with two attachment portions spaced from each other, which during normal use are connected to the sterilization container lid, is provided for attachment of the document. The clamping portion is located between the attachment portions, and a document receptacle is formed between the clamping portion and the upper side. The document to be attached can be inserted into the document receptacle and fixed therein in a clamped manner to the upper side by means of the clamping portion. By means of the document holder, it is, in particular, possible to also affix large documents, for example, in standard A4 format, to the upper side of the sterilization container lid. Such documents may contain comprehensive information for detailed labelling of the sterilization articles and/or of the sterilization container.

Documents arranged on the upper side of the sterilization container lid are spatially separate from functional elements such as, for example, handle elements or closure elements of the sterilization container. This facilitates the affixing of documents without affecting the handling of the further functional elements.

It is expedient if the clamping portion comprises a flat clamping element for surface-to-surface contacting of the document. The document can be attached more reliably by surface-to-surface securing. The extent of the flat clamping element is, for example, in at least one spatial direction, at least 3 millimeters, preferably at least 5 millimeters and, even more preferred, at least 10 millimeters. Such a clamping element may be produced, for example, in the form of a strip or a band, for example, from a flat material.

It is advantageous if the clamping portion comprises a clamping element which is arranged at a spacing from the upper side, and if at least one spacer element is arranged on the clamping element, by way of which the clamping element is supported on the upper side. The document receptacle can be formed with a defined size between the clamping portion and the upper side, and owing to the spacing of the clamping portion from the upper side, the document to be attached can be inserted into and removed from the document receptacle more easily.

The at least one spacer element is preferably configured as a tongue protruding resiliently from the clamping element. For example, the at least one spacer element is formed integrally with the clamping element, and, in particular, it can be configured so as to protrude from a plane defined by the clamping element. For this purpose, the at least one spacer element can be punched out of the clamping element and bent relative to it.

It is expedient if two spacer elements are provided, which are supported at or near opposite rim portions of a rim of the sterilization container lid on the upper side, and if the document receptacle is arranged between the spacer elements. This allows formation of a relatively large document receptacle, which extends from a rim portion or near to it to an opposite rim portion or near to it.

The clamping portion is expediently of straight-lined configuration, for example, owing to manufacture of the document holder from an elongate material, for example, a flat material.

In practice, it proves advantageous for the first attachment portion and/or the second attachment portion to be end portions of the document holder.

During normal use, the document holder is connected to the sterilization container lid, the document holder and the sterilization container lid having attachment elements which interact. The attachment elements may interact with force locking, positive locking and/or material locking.

For example, it is advantageous if at least one of the attachment portions is in engagement with the sterilization container lid with force locking and/or positive locking. In particular, a latching or a clamping engagement may be provided, with at least one of the attachment portions engaging around or engaging behind the sterilization container lid.

Preferably, at least one of the attachment portions is detachably connected to the sterilization container lid. This makes it possible to widen the document receptacle for simplified removal or attachment of the document. In particular, both attachment portions and, therefore, the document holder in its entirety, may be detachably connected to the sterilization container lid. This allows the document holder to be fitted only when required on the sterilization container lid when a document has to be attached. Otherwise, the document holder may remain detached from the sterilization container lid and be stored separately.

In a different advantageous embodiment of the medical document attachment device, it proves advantageous for at least one of the attachment portions to be non-detachably connected to the sterilization container lid.

It may, in particular, be provided that at least one of the attachment portions is integrally connected to the sterilization container lid, for example, by way of a film hinge, which enables pivoting of the document holder relative to the sterilization container lid.

All in all, it is expedient if at least one of the attachment portions is pivotably mounted on the sterilization container lid and is transferable from a released position in which the other attachment portion is not connected to the sterilization container lid to a closed position in which the other attachment portion is connected to the sterilization container lid. This allows the document receptacle to be widened, so that the document can be inserted into or removed from the document receptacle more easily. The attachment portion and the sterilization container lid may comprise or form interacting bearing elements for the pivotable mounting.

The pivot axis runs, for example, parallel to a plane defined by the upper side of the sterilization container lid and may, in particular, be horizontally aligned in relation to normal use of the sterilization container lid on the sterilization container.

It is advantageous if the sterilization container lid has a rim and if the first attachment portion and/or the second attachment portion is/are connected to the rim. The attachment of the document holder to the rim makes it possible to do without attachment elements on a cover wall of the sterilization container lid which comprises the upper side and to impart a simpler construction to the sterilization container lid. For example, the first attachment portion and/or the second attachment portion is/are in clamping engagement with the rim.

The clamping portion expediently extends over the upper side from a first rim portion to a second rim portion of the rim, which is located opposite the first rim portion. This allows formation of as large a document receptacle as possible between the clamping portion and the upper side.

It proves advantageous for the sterilization container lid to have a cover wall from which the rim protrudes at an angle, and for the first attachment portion and/or the second attachment portion to be connected to the side of the rim that is oriented away from the cover wall and to be supported thereon against movement in the direction towards the cover wall. Such a sterilization container lid is, for example, a so-called "slip lid" which can be slipped over a sterilization container tub of the sterilization container. In this embodiment, the rim may have at the side that is oriented away from the cover wall a free edge which interacts with the first and/or the second attachment portion. For example, the first and/or the second attachment portion can engage around or engage behind the free edge. In this way, it is possible to do without separate attachment elements on the sterilization container lid. By being supported against movement in the direction towards the cover wall, the document holder can be attached to the sterilization container lid in a constructionally simple and reliably clamping manner. It may also be provided that one of the attachment portions is firmly connected to the side of the rim that is oriented away from the cover wall, for example, is pivotably mounted thereon. The document holder can thus be pivoted beyond the upper side in order to widen the document receptacle for simplified attachment or removal of the document.

The first attachment portion and/or the second attachment portion expediently lie/lies at least in sections against the rim on the outside. The likelihood that a user will unintentionally contact the document holder and release it from the sterilization container lid is thereby reducible.

It may be provided that the rim has at least one recess into which an attachment portion attached to the rim enters. In particular, it is conceivable that the recess is of complementary configuration to the attachment portion, so that the attachment portion arranged in the recess is, in addition, in alignment with the rim. The unintentional releasing of the document holder from the sterilization container lid by the user can thereby be prevented to a large extent.

In a constructionally simple configuration of the document holder, it is expedient if at least one of the attachment portions is aligned at an angle to the clamping portion, preferably if both attachment portions are aligned at an angle to the clamping portion. In the latter case, it is expedient for the angles to be of equal measure. Due to bending of one of the attachment portions at an angle to the clamping portion, it is, for example, possible to form a document holder which can be connected in a constructionally simple way to a sterilization container lid comprising a cover wall and a rim spaced therefrom, as was explained hereinabove.

The document holder, in particular, of the embodiment last described above, may have a U-shaped configuration, with the attachment portions forming the "legs" of the U.

In an implementation of the document attachment device in practice, it proves expedient for the angle to be greater than 90°. For example, the angle is approximately 95° to approximately 100°.

The at least one attachment portion bent at an angle relative to the clamping portion is preferably connected at the side oriented away from the clamping portion to the sterilization container lid. For example, the attachment portion is in clamping engagement with the sterilization container lid, and, in particular, it may engage around or engage behind a rim of the sterilization container lid. It is also conceivable for the attachment portion to be pivotably mounted on the sterilization container lid, in particular, its rim.

It may be provided that the document holder is of rounded configuration in the area of the bending of the clamping portion and of the at least one attachment portion and can thus be adapted to a rounded contour of the sterilization container lid, which is rounded in the transition from a cover wall to a rim.

The above description, therefore, includes, in particular, a preferred embodiment of the document attachment device in accordance with the invention with a document holder, which is expediently of bracket-shaped configuration with a middle part forming the clamping portion and two legs aligned at an angle to the middle part and each forming an attachment portion, it being particularly preferred for the legs to be connected at the ends to a rim of the sterilization container lid, for example, by clamping engagement or pivotable mounting.

It is expedient if the at least one document holder is of symmetrical or substantially symmetrical configuration in relation to a plane of symmetry which coincides with a median longitudinal plane of the sterilization container lid when the document holder is connected. This makes it possible to connect the document holder in two different orientations to the sterilization container lid and, therefore, facilitates handling of the document attachment device.

Furthermore, the handling is expediently facilitated by the at least one document holder being of deformable construction and, in particular, elastically deformable. This makes it easier to release the document holder from and/or connect it to the sterilization container lid.

It has already been mentioned that the at least one document holder may be produced from a flat material, and the document holder may also consist of a flat material. Use of a flat material enables cost-effective manufacture of the document holder which, in addition, in a constructionally simple manner, may be configured so as to be deformable. The above-mentioned flat clamping element of the clamping portion is constructionally also easy to produce.

For example, the document holder consists of or is produced from a band-shaped or strip-shaped flat material.

Cost-effective manufacture is also enabled by the at least one document holder being of integral construction.

The at least one document holder is preferably produced from a sterilizable material.

The at least one document holder may be produced at least partially from metal. For example, the document holder is produced completely from metal, preferably from a metallic flat material, which expediently is elastically deformable.

The at least one document holder may also be produced at least partially or completely from plastic material, for example, polyphenylsulfone (PPSU).

It is advantageous if the at least one document holder comprises or forms a labelling area which includes information relating to the sterilization container and/or sterilization items accommodated therein. In addition to the document, the at least one document holder itself can thus include data. For example, the labelling area comprises a section of the clamping portion on which information is stored. The labelling area may be permanently or temporarily labelled with information which is changeable or not changeable. The information is preferably stored in an optically readable manner on the labelling area so that it can be more easily detected by a user. For example, an adhesive label is affixed to the labelling area on the document holder. There may also be an embossment of the document holder on the labelling area. The labelling area may, for example, be written on by hand with a pen or by machine, for example, using a laser. It is also conceivable for the document holder to be designed in its entirety as label carrier. Accordingly, it may be provided that the document holder is dyed, and the document attachment device comprises differently dyed document holders, depending on the kind of sterilization container or sterilization articles accommodated therein.

An advantageous embodiment of the document attachment device in accordance with the invention comprises more than one document holder. In particular, it is possible for more than only one document holder to be connected to the sterilization container lid for clamped fixing of the document.

The following description of a preferred embodiment of the invention serves in conjunction with the drawings to explain the invention in greater detail.

DETAILED DESCRIPTION OF THE INVENTION

Figure 1:
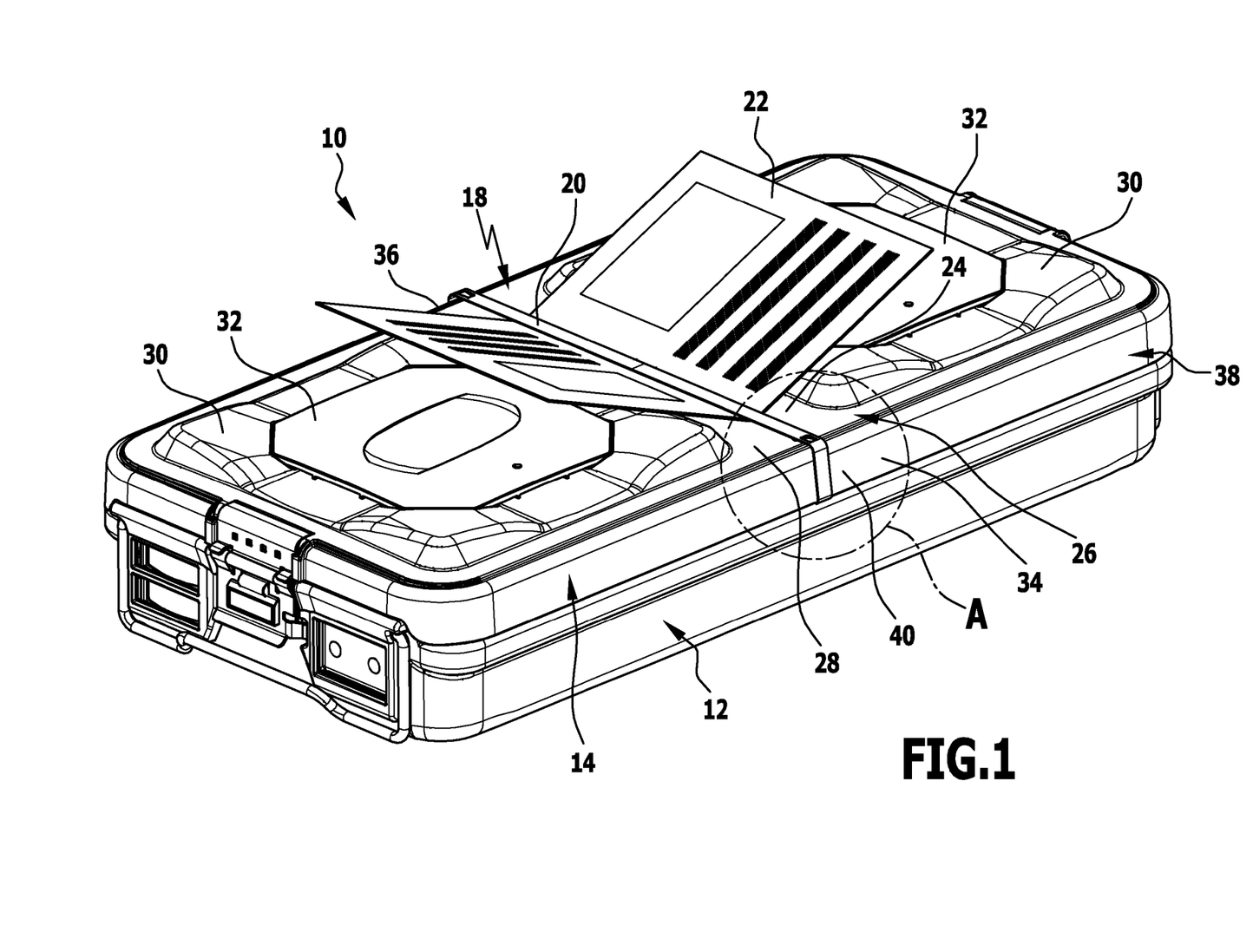
FIG. 1 shows a perspective representation of a medical sterilization container comprising a first preferred embodiment of a document attachment device in accordance with the invention including a sterilization container lid and a document holder, and of a document attached to the sterilization container lid.
Figure 4:
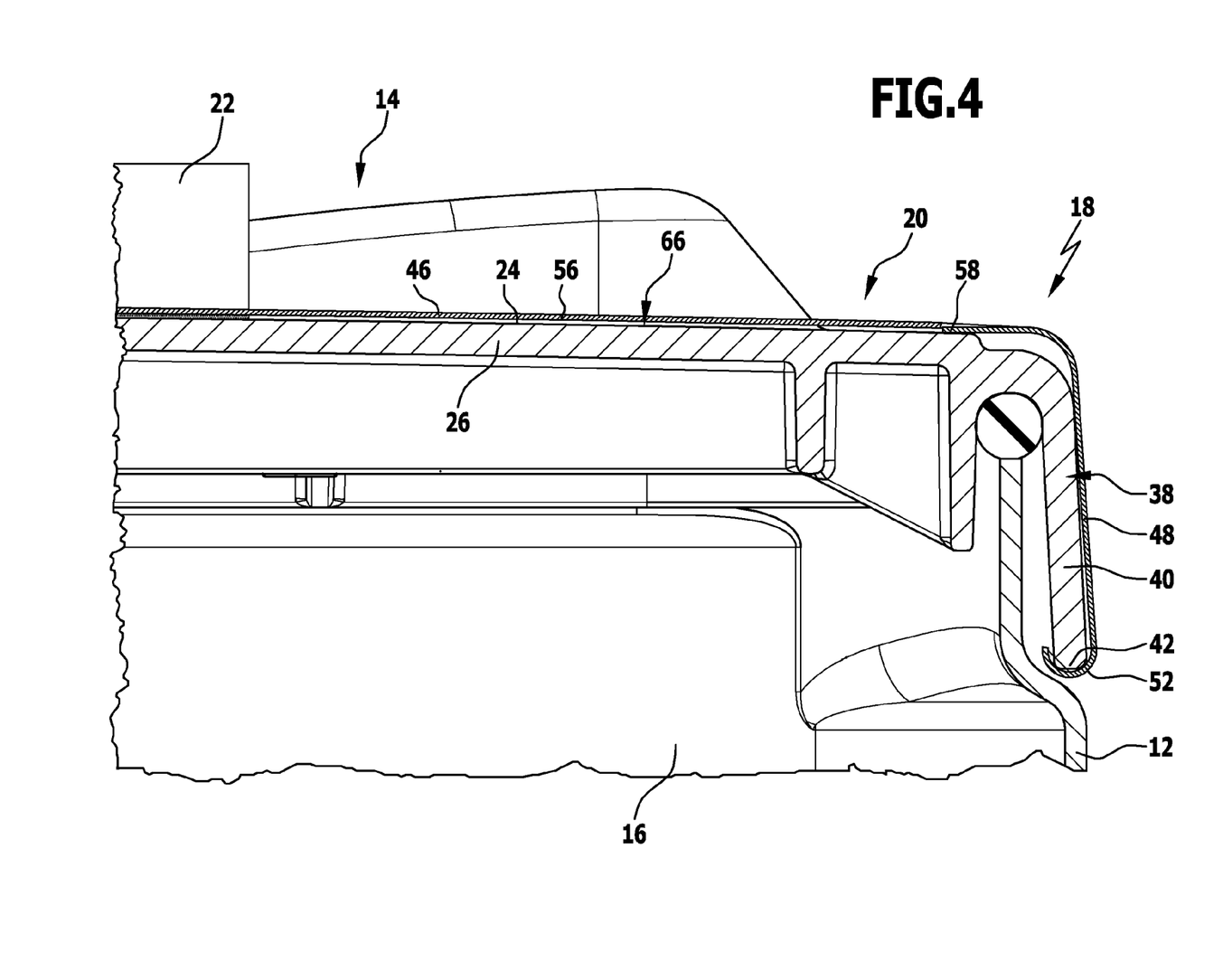
FIG. 4 shows a sectional representation (in part) in the area of detail A of the sterilization container from FIG. 1.

FIG. 1 shows in perspective representation a medical sterilization container denoted in its entirety by reference numeral 10. The sterilization container 10 comprises a sterilization container tub 12 and a sterilization container lid 14 which can be placed on and firmly connected to the sterilization container tub 12. The sterilization container tub 12 and the sterilization container lid 14 define between them a receiving space 16 for sterilization articles, not shown in the drawings, in particular, surgical instruments (FIG. 4). The sterilization articles can be accommodated in a medical perforated basket, also not shown in the drawings, which is placed in the receiving space 16.

The sterilization container 10 comprises a preferred embodiment of a medical document attachment device, denoted by reference numeral 18, which comprises in addition to the sterilization container lid 14 a document holder 20. The document holder 20 can interact with the sterilization container lid 14 for clamped attachment of a document 22 to an upper side 24 of the sterilization container lid 14, as will be explained hereinbelow. The document 22 may contain information on the sterilization container 10 and, in particular, on the sterilization articles accommodated in the receiving space 16.

Like the sterilization container 10 in its entirety, the sterilization container lid 14 is rectangular in a plan view, and it has a cover wall 26 defining the upper side 24. The cover wall 26 comprises a planar portion 28 defining a plane, and two portions 30 having elevations. Filter devices 32 are inserted in the portions 30 having elevations to enable the exchange of medium between the atmosphere and the receiving space 16 through the cover wall 26. The planar portion 28 extends, in particular, at the outer circumference of the cover wall 26 and in the area of the center of the cover wall 26 from a first longitudinal side 34 to an opposite longitudinal side 36 of the sterilization container lid 14.

The sterilization container lid 14 is configured as a slip lid, which can be slipped over the sterilization container tub 12. For this purpose, the sterilization container lid 14 comprises a circumferential rim 38, which protrudes at an angle from the cover wall 26 and engages over the free rim of the sterilization container tub 12 on the outside. The angle between the rim 38 and the cover wall 26 at its planar portion 28 is, in the present case, approximately 95°.

The rim 38 has, in particular, a first rim portion 40 at the longitudinal side 34 and a second rim portion at the longitudinal side 36. The second rim portion is not shown in the drawings. At the side oriented away from the cover wall 26, the rim 38 has in the region of the first rim portion 40 and the rim portion not shown, in each case, a free edge 42 (FIG. 4).

The sterilization container lid 14 is of overall symmetrical configuration in relation to a plane of symmetry, not shown in the drawings, which is a median longitudinal plane of the sterilization container lid 14 and the sterilization container 10 and which runs in the middle between the longitudinal sides 34 and 36 and is aligned perpendicularly to the planar portion 28.

Figure 2:
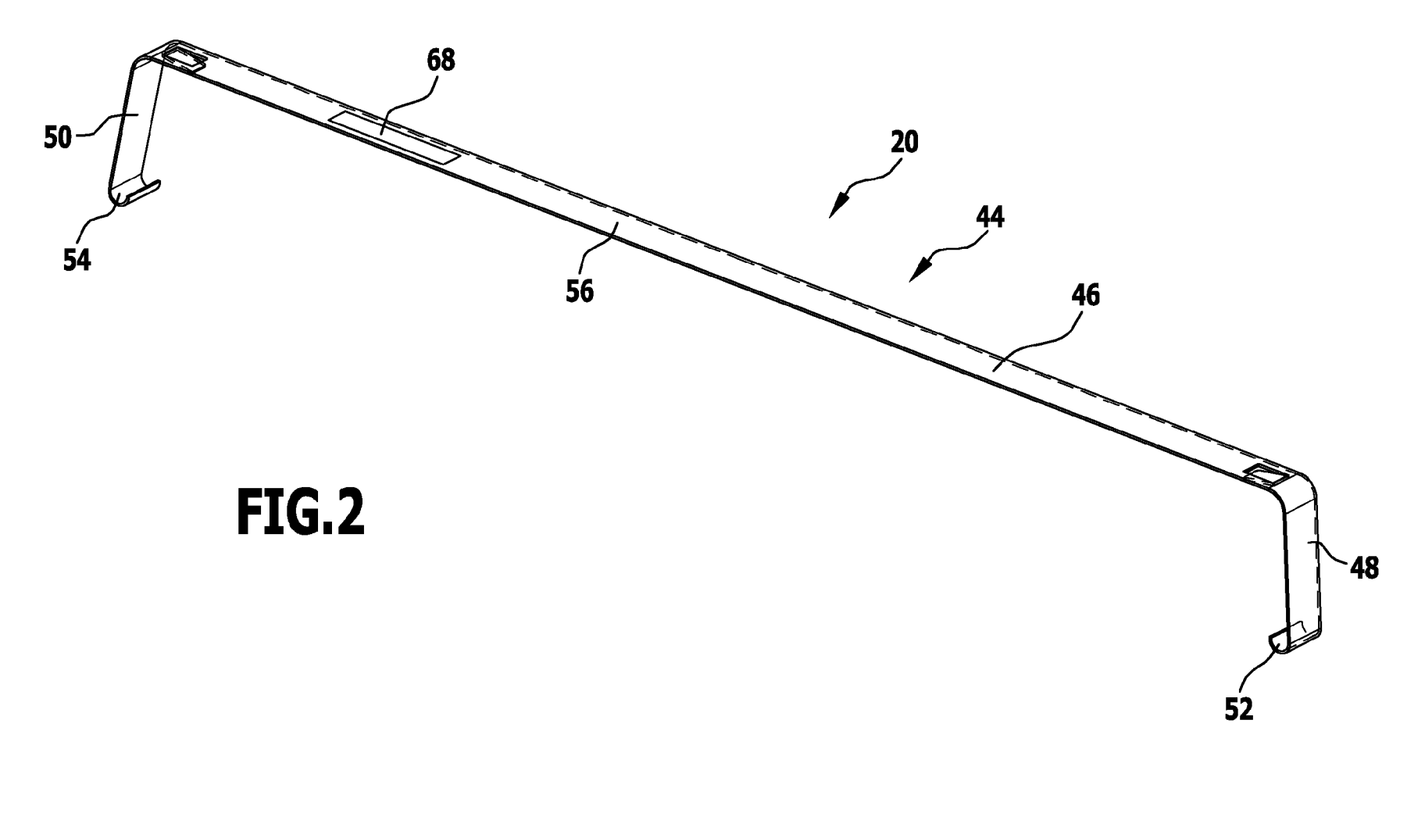
FIG. 2 shows a perspective representation of the document holder from FIG. 1.
Figure 3:
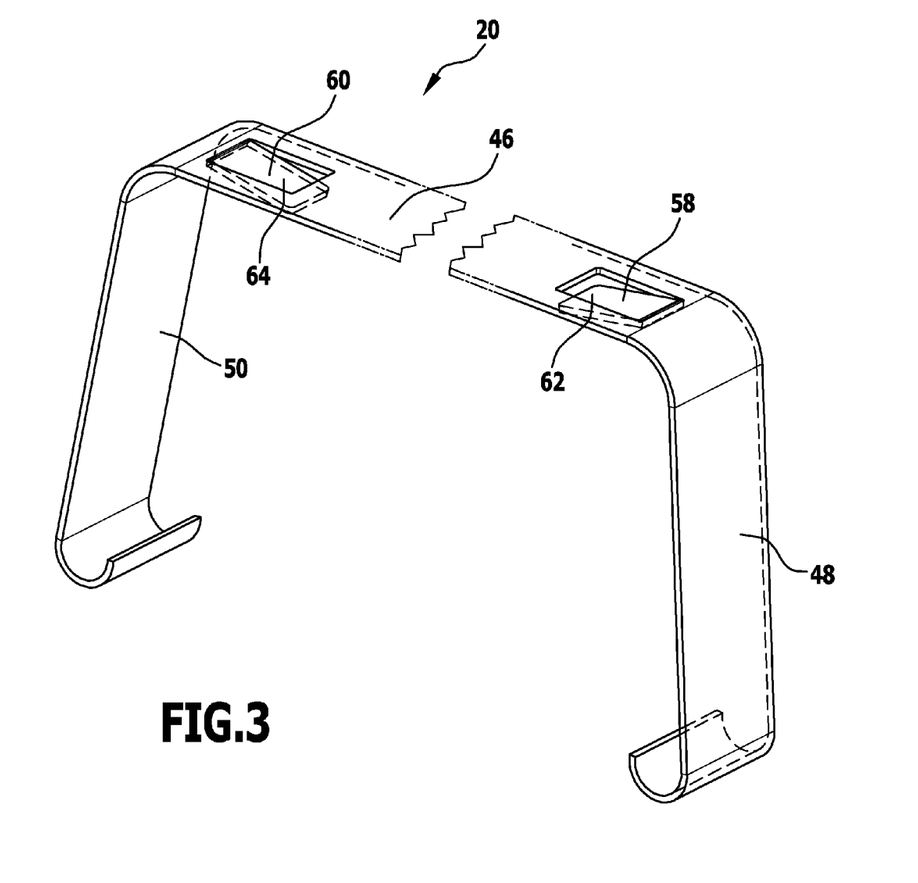
FIG. 3 shows an enlarged partial representation of the document holder from FIG. 1.

As is evident, in particular, from FIGS. 2 and 3, the document holder 20 is configured as a U-shaped bracket 44, which has a middle portion 46 and two end portions 48 and 50 protruding from the middle portion 46. The middle portion 46 is, as well as the end portions 48 and 50, unless explained otherwise hereinbelow, of planar configuration. Each of the end portions 48 and 50 protrudes from the middle portion 46 at an angle which, in the present case, is greater than 90°, for example, approximately 95° to approximately 100°, and, in particular, approximately 97°. The end portions 48 and 50 protrude from the middle portion 46 in directions facing away from each other, but they protrude from the same side of the middle portion 46. Areas of transition from the middle portion 46 to the end portions 48 and 50 are of rounded configuration and are adapted approximately to the rounded contour of the sterilization container lid in the area of transition from the cover wall 26 to the rim 38.

The free ends of the end portions 48 and 50, which are each arranged at their sides oriented away from the middle portion 46, are curved in the shape of hooks, more particularly, first in the direction of the respective other end portion 48, 50, and at their ends face in the direction of the middle portion 46. The free ends of the end portions 48 and 50 form attachment elements 52 and 54, respectively, for clamped fastening of the document holder 20 to the rim 38. For this reason, the end portions 48 and 50 are also referred to as attachment portions.

The middle portion 46 comprises a flat clamping element 56, which extends between the rounded areas of transition to the attachment portions 48, 50. The clamping element 56 serves to fix the document 22 in a clamped manner to the upper side 24. For this reason the middle portion 46 is also referred to as clamping portion.

The document holder 20 further comprises two spacer elements 58 and 60, which protrude from the plane defined by the clamping element 56 in the direction of the upper side 24. The spacer elements 58 and 60 are arranged immediately adjacent to the rounded areas of transition to the attachment portions 48 and 50, respectively, and are configured as resilient tongues 62 and 64, respectively, protruding from the clamping element 56. By way of the spacer elements 58 and 60, the clamping element 56 can be supported on the upper side of the cover wall 26 near the rim portions of the rim 38.

The document holder 20 is made of a sterilizable material. Furthermore, the document holder 20 is mainly made of an elastically deformable material. For example, the document holder 20 is made of a metal, in particular, stainless steel, but it is also possible for it to be made of a plastic material, for example, polyphenylsulfone (PPSU).

In particular, the document holder 20 is, in the present case, of flat configuration, if the bending of the attachment portions 48 and 50 relative to the clamping portion 46, their curvature at the attachment elements 52 and 54 and the bent resilient tongues 62 and 64 are disregarded. This makes it possible, for example, to produce the document holder 20 from a flat material such as a deformable sheet of metal. The attachment portions 48 and 50 can then be bent relative to the clamping portion 46, the attachment elements 52 and 54 can be bent at the free ends of the attachment portions 48 and 50, respectively. The tongues 62 and 64 can be punched out of the clamping element 56 and bent relative to it.

The clamping element 56 is, in the present case, flat with an extent in the transverse direction of at least approximately 3 millimeters. In the present case, the clamping element 56 is at least approximately 10 millimeters wide in the transverse direction. In the preferred embodiment of the document attachment device 18 shown in the drawings, this corresponds to the total width of the document holder 20 which, therefore, overall has the shape of a deformed strip of material. In the longitudinal direction, the clamping element 56 extends from the first rim portion 40 to the second rim portion, not shown, transversely across the cover wall 26 when the document holder 20, as explained hereinbelow, is attached in accordance with the intended use to the sterilization container lid 14.

To attach the document holder 20 to the sterilization container lid 14, the hook-shaped attachment elements 52 and 54 can be brought into engagement with the rim portion 40 and the opposite rim portion (FIG. 4). For example, the document holder 20 is placed from above on the sterilization container lid 14, and the clamping portion 46 can be deformed and/or the attachment portions 48 and 50 can be spread out relative to the clamping portion 46. By applying force in the direction of the cover wall 26, the hook-shaped attachment elements 52 and 54 can be moved along the outside of the rim 38 until the attachment elements 52 and 54 enter into engagement with the free edge 42 and the free edge not shown at the opposite rim portion. The attachment portions 48 and 50 thereby engage around the free edge 42 and the free edge not shown, so that the document holder 20 is supported on the rim 38 against movement in the direction of the cover wall 26. When the attachment portions 48 and 50 engage the rim 38, the document holder 20 undergoes deformation again into its original shape. At the same time, the clamping portion 46 is supported resiliently on the cover wall 26 by way of the resilient tongues 62 and 64, so that the document holder 20 is clamped to the sterilization container lid 14. In the connected state, the document holder 20 engages over the sterilization container lid 14 and engages under, in particular, engages around, the rim 38, so that it is held reliably on the sterilization container lid 14.

The document holder 20 can be connected to the sterilization container lid 14 in a different way, for example, by the attachment portion 48 first engaging around the free edge 42 and the document holder 20 then being pivoted relative to the sterilization container lid until the attachment portion 50 with the attachment element 54 also engages around the free edge opposite the free edge 42, or vice versa.

Ideally, the document holder 20 will be attached to the sterilization container lid 14 in such a way that it extends transversely to its longitudinal direction between the elevated portions 30.

A document receptacle 66 in which the document 22 can be fixed in a clamped manner to the sterilization container lid 14 is formed between the clamping element 56 and the upper side 24. The document receptacle extends between the tongues 62 and 64 and, therefore, in the transverse direction of the sterilization container lid 14 essentially over the entire transverse side thereof.

The provision of the resilient tongues 62 and 64 serves not only to improve fixing of the document holder 20 owing to the resilient force of the tongues 62 and 64. The tongues 62 and 64 also allow expansions of the document receptacle 66 which occur when fixing documents 22 of different thicknesses to be compensated. In particular, relatively thick documents 22 can also be fixed without the document holder 20 undergoing permanent deformation as the differences in thickness can be compensated by the elastically resilient tongues 62 and 64.

The clamped fixing of documents 22 to the upper side 24 of the sterilization container lid 14 by means of the document holder 20 is easy to manage, and, in particular, it is possible to even fix large documents containing comprehensive information relating to the sterilization container 10 and sterilization articles accommodated therein. For example, the document 22 shown in the drawings is a list of sterilization items in standard A4 format.

The fixing of the document 22 to the upper side 24 also makes labelling of the sterilization container 10 and/or sterilization articles at one of the end faces of the sterilization container tub 12, as is the case in the conventional sterilization containers, unnecessary. This facilitates the handling of documents for labelling and, in particular, avoids interference with the handling of handle elements and/or closure elements arranged at the end faces for fixing the sterilization container lid 14 to the sterilization container tub 12.

The small space between the upper side 24 and the clamping element 56 facilitates insertion of the document 22 into and removal of the document 22 from the document receptacle 66 when the document holder 20 is already connected to the sterilization container lid 14. Alternatively, when connecting the document holder 20 to the sterilization container lid 14, the document holder 20 can be positioned over the document 22 and connected to the sterilization container lid 14, with the document 22 being fixed at the same time. To remove the document 22, the document holder 20 could be released from the sterilization container lid 14.

To release the document holder 20, the user can disengage the attachment portions 48 and 50 from the rim 38 and lift up the document holder 20. It is also conceivable for only one of the attachment portions 48 or 50 to be disengaged from the rim 38, whereupon the document holder 20 is pivoted at the sterilization container lid 14 in order to subsequently disengage the other one of the attachment portions 48, 50 from the rim 38.

Owing to the possibility of releasing the document holder 20, it can be stored separately from the sterilization container lid 14 if a document 22 is not to be fixed to the sterilization container lid 14. However, the document holder 20 may also remain on the sterilization container lid 14, as it is sterilizable and is not affected by the sterilization operation.

It may be provided that the document attachment device 18 comprises a plurality of document holders which, in particular, may be identical in configuration to the document holder 20.

The document holder 20 comprises a labelling area 68 (FIG. 2), which, in the present case, is an optical labelling area. Optically readable information relating to the sterilization container 10 and/or sterilization articles accommodated therein is arranged or can be arranged on the labelling area 68. For example, the labelling area 68 comprises an embossment of the clamping element 56. A label, for example, in the form of an adhesive label, which can be written on by hand with a pen or by a machine, for example, with a laser, may be provided on the labelling area 68. A label including a machine-readable code, for example, a bar code, is also conceivable.

Apart from the labelling area 68, the document holder 20 is of symmetrical configuration. When connected to the sterilization container lid 14 during normal use, it is of symmetrical configuration in relation to the above-mentioned median longitudinal plane. This facilitates handling of the document holder 20, which can be attached in two different orientations to the sterilization container lid 14.

Figure 5:
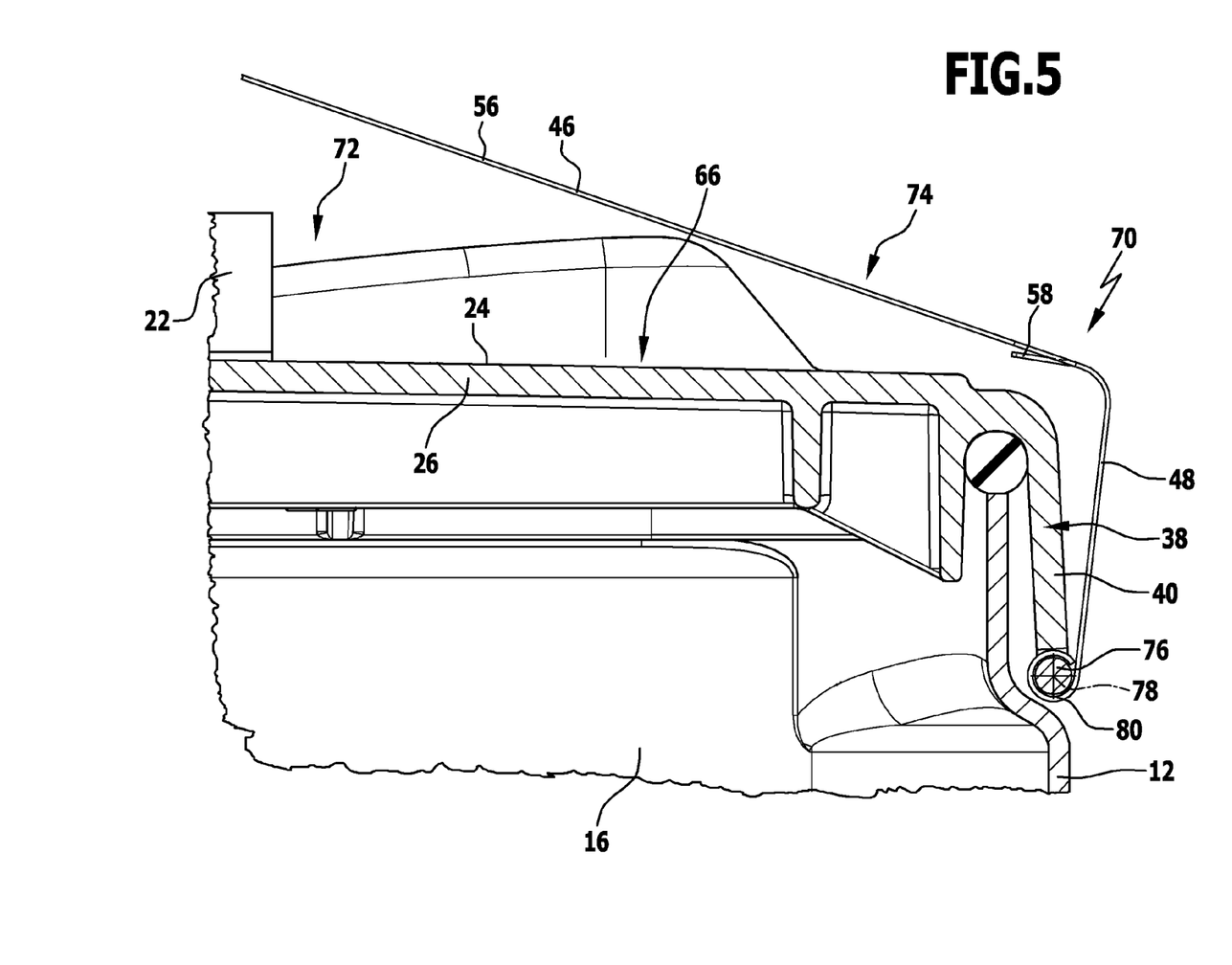
FIG. 5 shows a representation corresponding to FIG. 4, in which the sterilization container comprises a second preferred embodiment of a document attachment device in accordance with the invention, the document holder of which assumes a released position relative to the sterilization container lid.

A second preferred embodiment of a document attachment device denoted by reference numeral 70 is discussed hereinbelow with reference to FIG. 5. The document attachment device 70 comprises a sterilization container lid 72 and a document holder 74, which are of largely identical configuration to the sterilization container lid 14 and the document holder 20, respectively. The same reference numerals are used for features and components of the document attachment devices 18 and 70, which are the same and function in the same way, and only the essential differences will be discussed hereinbelow.

The sterilization container lid 72 comprises at the rim portion 40 in the area of the free edge 42 a bearing element 76 in the form of a bearing journal which defines a pivot axis 78. The pivot axis 78 is aligned parallel to the plane defined by the planar portion 28 and during normal use of the sterilization container lid 72 can, in particular, be horizontally aligned with the sterilization container tub 12.

The attachment portion 48 of the document holder 74 also comprises a bearing element 80 at the free end oriented away from the clamping portion 46. The bearing element 80 is configured as an eyelet which interacts with the bearing element 76 and by way of which the document holder 74 is firmly connected to the rim 38. The interacting bearing elements 76 and 80 enable a pivotable bearing of the document holder 74 on the rim 38. This allows the document holder 74 to be transferred from a released position shown in FIG. 5 to a closed position not shown in the drawings. In the released position, the document receptacle 66 is widened to such an extent that the user can easily insert the document 22 into or remove the document 22 from the document receptacle 66. In the closed position, the attachment portion 50 interacts with the free edge at the rim portion, not shown, located opposite the rim portion 40, and it is in clamping engagement with this rim portion, as was explained above by way of the example of the attachment portion 48 and the rim portion 40 (FIG. 4). In the closed position, the clamping portion 46 of the document holder 74 assumes the same position relative to the cover wall 26 as was explained above by way of the example of the clamping portion 46 of the document holder 20 (FIG. 4), with the document 22 fixed in a clamped manner to the upper side 24.

Instead of the pivotable bearing of the document holder 74 by way of interacting bearing elements 76 and 80, an integral connection of a document holder to a sterilization container lid by means of a film hinge, so that the document holder is of pivotable construction relative to the sterilization container lid, could also be provided.

The invention claimed is:

1. Medical document attachment device for a medical sterilization container, comprising:
   a sterilization container lid comprising a cover wall defining an upper side of the sterilization container lid,
   at least one document holder having a first attachment portion and spaced therefrom a second attachment portion,
   a clamping portion arranged between the first attachment portion and the second attachment portion,
   the first attachment portion and the second attachment portion being fixed to the sterilization container lid when the document holder is connected to the sterilization container lid, and
   a document receptacle formed between the clamping portion and the upper side of the sterilization container lid in which a document is fixable in a clamped manner by means of the clamping portion on the upper side, wherein:

the sterilization container lid has a rim, the rim protrudes at an angle from the cover wall, at least one of the first attachment portion and the second attachment portion engages under a distal edge of a side of the rim that is oriented away from the cover wall and is supported thereon against movement in a direction towards the cover wall, the clamping portion comprises a clamping element which is arranged at a spacing from the upper side, and at least one spacer element is arranged on the clamping element, by way of which the clamping element is supported on the upper side, and the at least one spacer element is configured as a tongue protruding resiliently from the clamping element.

2. Document attachment device in accordance with claim 1, wherein the clamping element comprises a flat clamping element for surface-to-surface contacting of the document.

3. Document attachment device in accordance with claim 1, wherein the at least one spacer element comprises two spacer elements, which are supported at or near opposite rim portions of the rim on the upper side, and the document receptacle is arranged between the spacer elements.

4. Document attachment device in accordance with claim 1, wherein at least one of the first attachment portion and the second attachment portion is an end portion of the document holder.

5. Document attachment device in accordance with claim 1, wherein at least one of the attachment portions is in engagement with the sterilization container lid with at least one of a force locking and a positive locking connection.

6. Document attachment device in accordance with claim 1, wherein at least one of the attachment portions is detachably connected to the sterilization container lid.

7. Document attachment device in accordance with claim 1, wherein at least one of the attachment portions is non-detachably connected to the sterilization container lid.

8. Document attachment device in accordance with claim 7, wherein at least one of the attachment portions is integrally connected to the sterilization container lid.

9. Document attachment device in accordance with claim 1, wherein at least one of the attachment portions is pivotably mounted on the sterilization container lid and is transferable from a released position in which the other attachment portion is not connected to the sterilization container lid to a closed position in which the other attachment portion is connected to the sterilization container lid.

10. Document attachment device in accordance with claim 1, wherein the clamping portion extends over the upper side from a first rim portion to a second rim portion of the rim, which is located opposite the first rim portion.

11. Document attachment device in accordance with claim 1, wherein at least one of the first attachment portion and the second attachment portion lies against the rim on the outside.

12. Document attachment device in accordance with claim 1, wherein at least one of the attachment portions is aligned at an angle to the clamping portion.

13. Document attachment device in accordance with claim 1, wherein both attachment portions are aligned at an angle to the clamping portion.

14. Document attachment device in accordance with claim 12, wherein the angle is greater than 90°.

15. Document attachment device in accordance with claim 12, wherein the at least one attachment portion is bent at an angle relative to the clamping portion and is connected at the side oriented away from the clamping portion to the sterilization container lid.

16. Document attachment device in accordance with claim 1, wherein the at least one document holder is of bracket-shaped configuration with a middle part forming the clamping portion and two legs aligned at an angle to the middle part, each of the legs forming an attachment portion.

17. Document attachment device in accordance with claim 1, wherein the at least one document holder is of symmetrical or substantially symmetrical configuration in relation to a plane of symmetry which coincides with a median longitudinal plane of the sterilization container lid when the document holder is connected.

18. Document attachment device in accordance with claim 1, wherein the at least one document holder is of deformable construction.

19. Document attachment device in accordance with claim 1, wherein the at least one document holder consists of or is produced from a flat material.

20. Document attachment device in accordance with claim 1, wherein the at least one document holder is of integral construction.

21. Document attachment device in accordance with claim 1, wherein the at least one document holder is produced from a sterilizable material and/or at least partially from metal and/or partially from plastic material.

22. Document attachment device in accordance with claim 1, wherein the at least one document holder comprises more than one document holder.

23. Medical document attachment device for a medical sterilization container, comprising:

a sterilization container lid comprising a cover wall defining an upper side of the sterilization container lid, at least one document holder having a first attachment portion and spaced therefrom a second attachment portion, a clamping portion arranged between the first attachment portion and the second attachment portion, the first attachment portion and the second attachment portion being fixed to the sterilization container lid when the document holder is connected to the sterilization container lid, and a document receptacle formed between the clamping portion and the upper side of the sterilization container lid in which a document is fixable in a clamped manner by means of the clamping portion on the upper side, wherein:

the sterilization container lid has a rim, the rim protrudes at an angle from the cover wall, at least one of the first attachment portion and the second attachment portion engages under a distal edge of a side of the rim that is oriented away from the cover wall and is supported thereon against movement in a direction towards the cover wall, the clamping portion comprises a clamping element which is arranged at a spacing from the upper side, and at least one spacer element is arranged on the clamping element, by way of which the clamping element is supported on the upper side, and the at least one spacer element comprises two spacer elements, which are supported at or near opposite rim portions of the rim on the upper side, and the document receptacle is arranged between the spacer elements.

* * * * *